(12) United States Patent
Kawanishi

(10) Patent No.: US 11,759,163 B2
(45) Date of Patent: Sep. 19, 2023

(54) RADIATION IMAGING SYSTEM, CONTROL APPARATUS, CONTROL METHOD OF RADIATION IMAGING SYSTEM, AND STORAGE MEDIUM

(71) Applicant: CANON KABUSHIKI KAISHA, Tokyo (JP)

(72) Inventor: Tomohiro Kawanishi, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 148 days.

(21) Appl. No.: 17/359,269

(22) Filed: Jun. 25, 2021

(65) Prior Publication Data

US 2021/0401393 A1    Dec. 30, 2021

(30) Foreign Application Priority Data

Jun. 30, 2020 (JP) .................................. 2020-113190

(51) Int. Cl.
*A61B 6/00* (2006.01)
*G06T 7/00* (2017.01)

(52) U.S. Cl.
CPC ................ *A61B 6/54* (2013.01); *A61B 6/482* (2013.01); *A61B 6/505* (2013.01); *A61B 6/582* (2013.01); *G06T 7/0014* (2013.01); *G06T 2207/10116* (2013.01); *G06T 2207/30008* (2013.01)

(58) Field of Classification Search
CPC ........... A61B 6/54; A61B 6/482; A61B 6/505; A61B 6/582; A61B 6/5258; A61B 6/586; A61B 6/54488; A61B 6/56; A61B 6/58; A61B 2560/0266; G06T 2207/10116; G06T 7/0014; G06T 2207/30008; H05G 1/36

See application file for complete search history.

(56) References Cited

U.S. PATENT DOCUMENTS

| 2014/0014828 | A1* | 1/2014 | Bredno ................. A61B 6/037 250/252.1 |
| 2017/0188443 | A1* | 6/2017 | Nakahara ................. A61B 6/40 |
| 2018/0064410 | A1* | 3/2018 | Li ......................... A61B 6/582 |

FOREIGN PATENT DOCUMENTS

JP        2013150762 A        8/2013

* cited by examiner

*Primary Examiner* — David P Porta
*Assistant Examiner* — Mamadou Faye
(74) *Attorney, Agent, or Firm* — Canon U.S.A., Inc. IP Division

(57) ABSTRACT

A radiation imaging system operable to generate a plurality of radiation images based on different radiation energies, comprises: a communication unit configured to obtain at set communication intervals a temperature of a radiation tube by communication with a radiation generating unit; and a control unit configured to control, based on comparison of the temperature obtained at the communication intervals and a change rate of the temperature and respectively set threshold ranges, an operation for maintaining a driving state of the radiation tube or execution of image processing for obtaining a substance amount of a substance that forms an object using the plurality of radiation images.

20 Claims, 6 Drawing Sheets

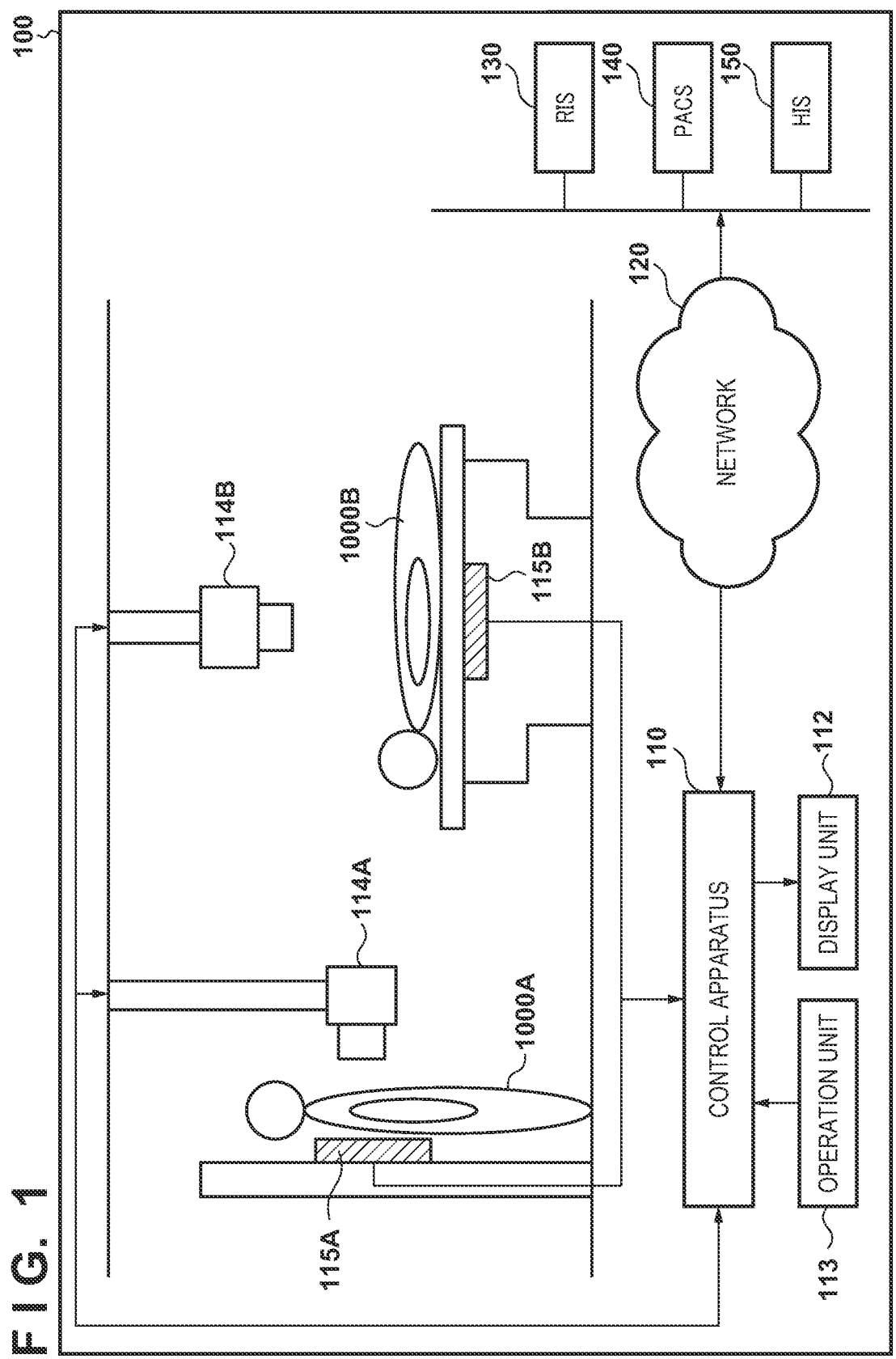

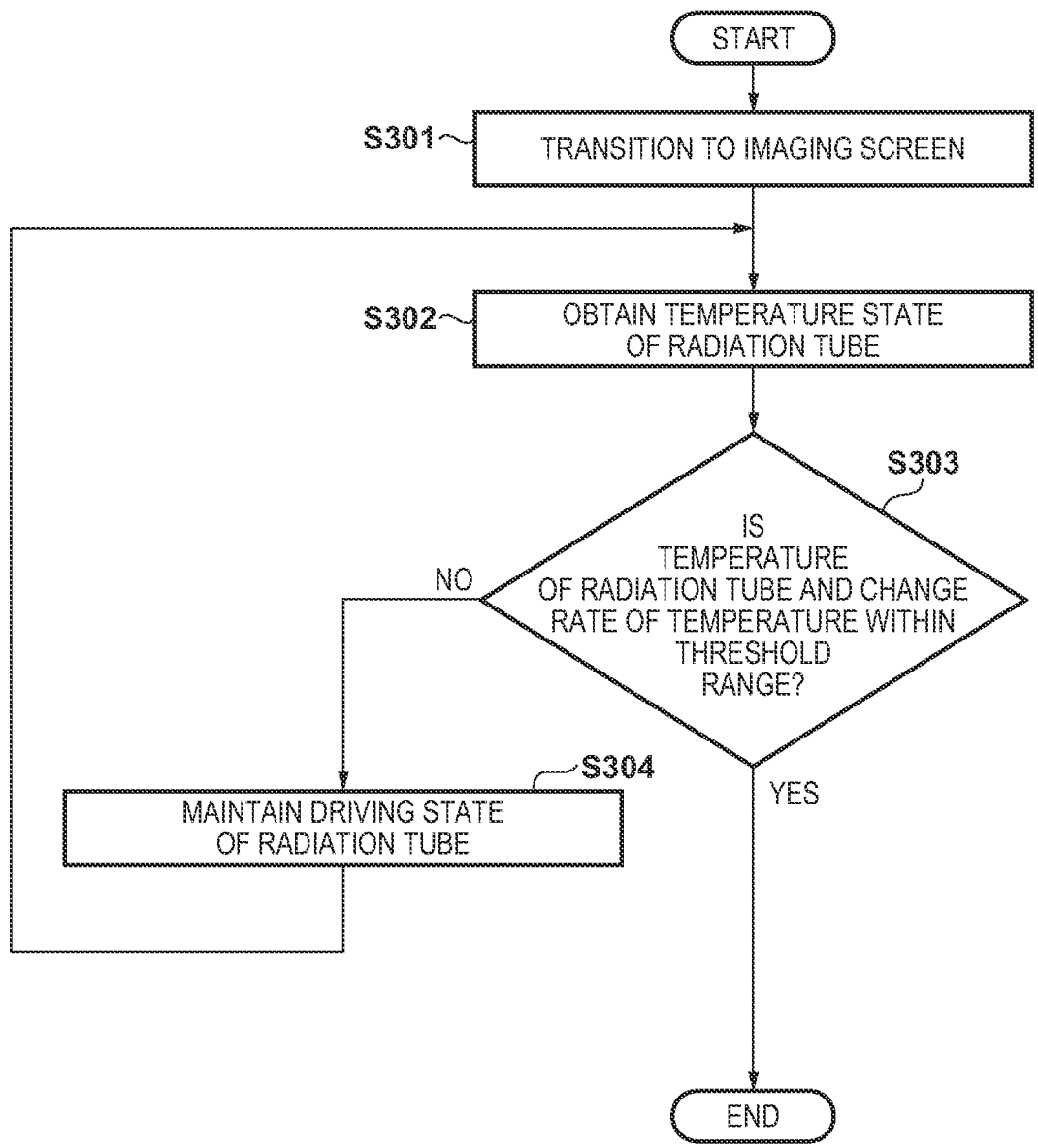

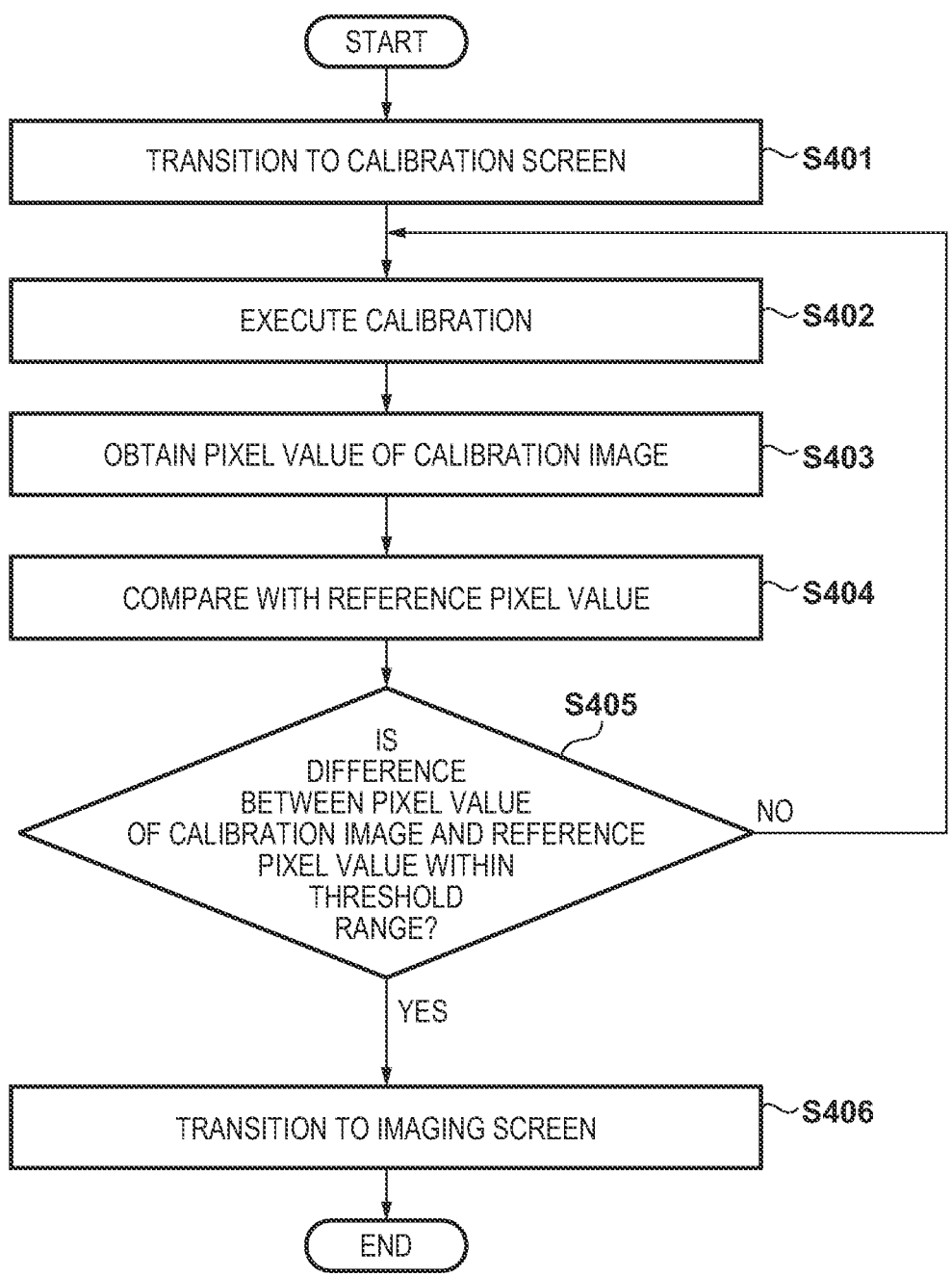

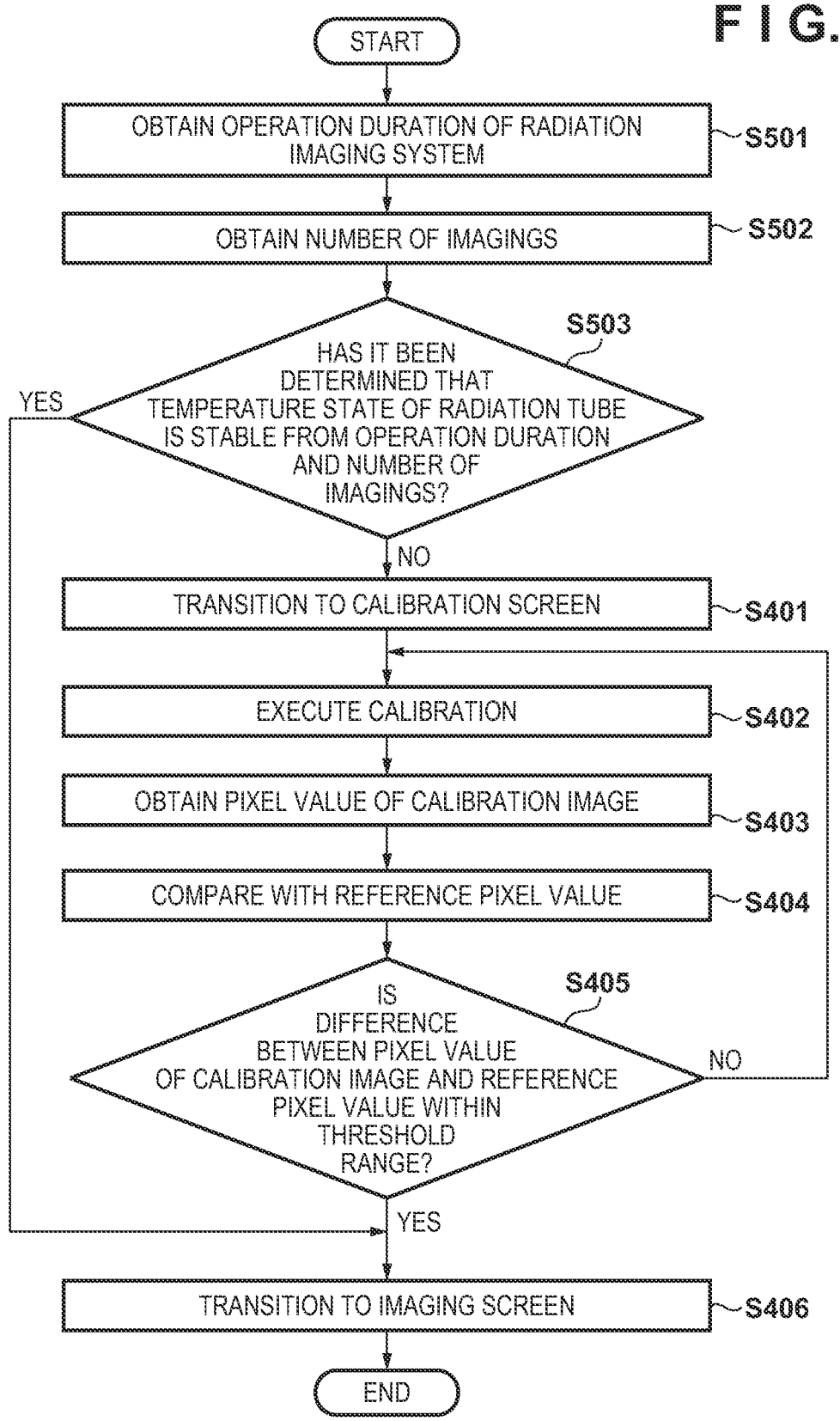

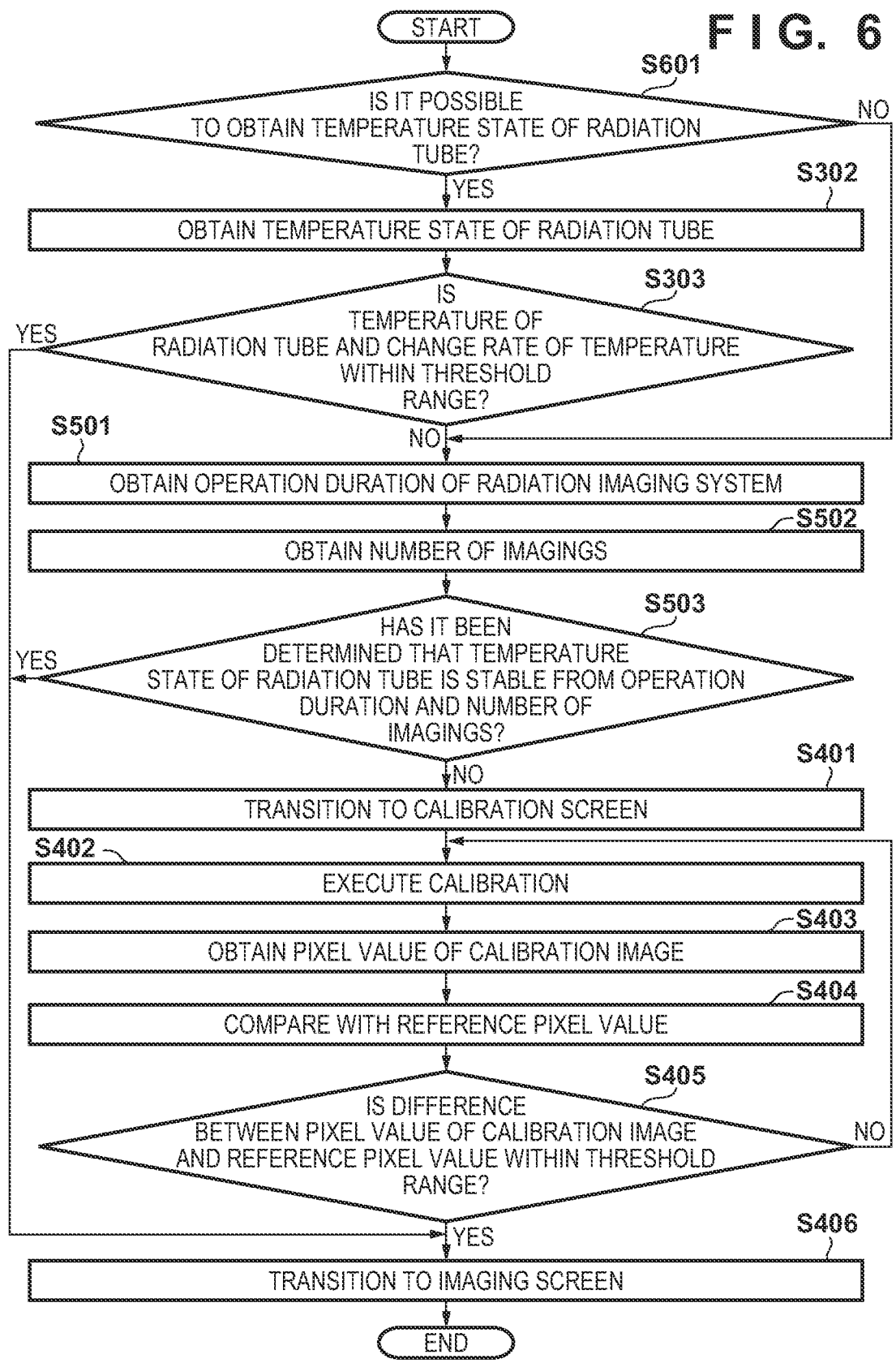

RADIATION IMAGING SYSTEM, CONTROL APPARATUS, CONTROL METHOD OF RADIATION IMAGING SYSTEM, AND STORAGE MEDIUM

BACKGROUND

Field of the Disclosure

The present disclosure relates to a radiation imaging system for performing radiation image imaging using energy subtraction, a control apparatus, a control method of the radiation imaging system, and a storage medium.

Description of the Related Art

Conventionally, as measuring of a substance amount that is obtained by image processing of a radiation image obtained using energy subtraction, measuring of a bone mineral amount in bone for diagnosing osteoporosis and the like is known. As methods of measuring a bone mineral amount, a DIP (Digital Image Processing; hereinafter, "DIP method") method and a DXA (Dual-energy X-ray Absorptiometry; hereinafter, "DXA method") method are used.

In measuring of bone density by the DIP method or the DXA method, it is necessary to capture minute change over time; however, in a case where a difference occurs in the pixel value of an obtained radiation image due to a difference in the temperature state of a radiation tube at a time of X-ray irradiation, accuracy of a measurement result will be affected.

For example, Japanese Patent Laid-Open No. 2013-150762 discloses, in a case where, due to a change over time in a characteristic of a radiation tube, imaging is not under imaging conditions in which a tube voltage is a standard, correcting a captured image or a bone mineral amount analysis result to obtain a bone mineral amount measurement result so as to correspond to imaging performed under standard imaging conditions.

However, in the method described in patent literature 1, in order to obtain a bone mineral amount with generality, it is necessary to sequentially change, in advance, imaging conditions to a plurality of conditions that include a reference imaging condition, and every time, obtain a radiation image of a reference substance, and obtain from these obtained radiation images, for each of the previously-described plurality of imaging condition combinations, a density gradient that relates to at least two portions in which the radiation transmission characteristics of the reference substance are mutually different.

Accordingly, for every imaging, it is necessary to obtain and calculate information that is necessary for correction and, if necessary, perform correction processing, and there may arise a case where efficiency of a bone mineral amount measurement flow decreases.

SUMMARY

Accordingly, in the present disclosure, a radiation imaging technique that is capable of reducing an effect on the measurement accuracy of a substance amount obtained by image processing based on radiation images that may be caused by a difference in the temperature state of a radiation tube is provided.

According to one aspect of the present disclosure, there is provided a radiation imaging system operable to generate a plurality of radiation images based on different radiation energies, the system comprising: a communication unit configured to obtain at set communication intervals a temperature of a radiation tube by communication with a radiation generating unit; and a control unit configured to control, based on comparison of the temperature obtained at the communication intervals and a change rate of the temperature and respectively set threshold ranges, an operation for maintaining a driving state of the radiation tube or execution of image processing for obtaining a substance amount of a substance that forms an object using the plurality of radiation images.

According to another aspect of the present disclosure, there is provided a radiation imaging system operable to perform image processing based on a plurality of radiation images based on different radiation energies, the system comprising: an image obtaining unit configured to obtain a pixel value of a calibration image generated by calibration of the radiation imaging system; and a control unit configured to, based on comparison of a difference between the pixel value of the calibration image and the pixel value of a reference image and a threshold range set for determining whether a temperature state of a radiation tube is stable, controls continuation of calibration execution or execution of image processing for obtaining an amount of a substance that forms an object using a plurality of radiation images.

According to still another aspect of the present disclosure, there is provided a radiation imaging system operable to generate a plurality of radiation images based on different radiation energies, the system comprising: a status obtaining unit configured to obtain current operation information of the radiation imaging system; a storage unit configured to store past operation information of the radiation imaging system; and a control unit configured to, in a statistical distribution that indicates operation information variability obtained by performing statistical processing on the past operation information, determines whether the current operation information is included in a statistical distribution threshold range in which a temperature state of a radiation tube is stabilized, and in a case where the current operation information is included in threshold range, uses the plurality of radiation images to execute image processing for obtaining an amount of a substance forming an object.

According to yet another aspect of the present disclosure, there is provided a control apparatus operable to control a radiation imaging system for generating a plurality of radiation images based on different radiation energies, the system comprising: a communication unit configured to obtain at set communication intervals a temperature of a radiation tube by communication with a radiation generating unit; and a control unit configured to control, based on comparison of the temperature obtained at the communication intervals and a change rate of the temperature and respectively set threshold ranges, an operation for maintaining a driving state of the radiation tube or execution of image processing for obtaining a substance amount of a substance that forms an object using the plurality of radiation images.

According to still yet another aspect of the present disclosure, there is provided a control apparatus operable to control a radiation imaging system that performs image processing based on a plurality of radiation images based on different radiation energies, the control apparatus comprising: an image obtaining unit configured to obtain a pixel value of a calibration image generated by calibration of the radiation imaging system; and a control unit configured to, based on comparison of a difference between the pixel value of the calibration image and the pixel value of a reference image and a threshold range set for determining whether a temperature state of a radiation tube is stable, controls continuation of calibration execution or execution of image processing for obtaining an amount of a substance that forms an object using a plurality of radiation images.

According to yet still another aspect of the present disclosure, there is provided a control apparatus operable to control a radiation imaging system for generating a plurality of radiation images based on different radiation energies, the system comprising: a status obtaining unit configured to obtain current operation information of the radiation imaging system; a storage unit configured to store past operation information of the radiation imaging system; and a control unit configured to, in a statistical distribution that indicates operation information variability obtained by performing statistical processing on the past operation information, determines whether the current operation information is included in a statistical distribution threshold range in which a temperature state of a radiation tube is stabilized, and in a case where the current operation information is included in threshold range, uses the plurality of radiation images to execute image processing for obtaining an amount of a substance forming an object.

According to still yet another aspect of the present disclosure, there is provided a method for controlling a radiation imaging system operable to generate a plurality of radiation images based on different radiation energies, the method comprising: obtaining at set communication intervals a temperature of a radiation tube by communication with a radiation generating unit; and controlling, based on comparison of the temperature obtained at the communication intervals and a change rate of the temperature and respectively set threshold ranges, an operation for maintaining a driving state of the radiation tube or execution of image processing for obtaining a substance amount of a substance that forms an object using the plurality of radiation images.

According to yet still another aspect of the present disclosure, there is provided a method for controlling a radiation imaging system for performing image processing based on a plurality of radiation images based on different radiation energies, the method comprising: obtaining a pixel value of a calibration image generated by calibration of the radiation imaging system; and based on comparison of a difference between the pixel value of the calibration image and the pixel value of a reference image and a threshold range set for determining whether a temperature state of a radiation tube is stable, controls continuation of calibration execution or execution of image processing for obtaining an amount of substance that forms an object using a plurality of radiation images.

According to still yet another aspect of the present disclosure, there is provided a method for controlling a radiation imaging system operable to generate a plurality of radiation images based on different radiation energies, the method comprising: obtaining current operation information of the radiation imaging system; storing, in a storage unit, past operation information of the radiation imaging system; and in a statistical distribution that indicates operation information variability obtained by performing statistical processing on the past operation information, determining whether the current operation information is included in a statistical distribution threshold range in which a temperature state of a radiation tube is stabilized, and in a case where the current operation information is included in threshold range, using the plurality of radiation images to execute image processing for obtaining an amount of a substance forming an object.

According to yet still another aspect of the present disclosure, there is provided a storage medium storing a program for causing a computer to function as each unit of a radiation imaging system operable to generate a plurality of radiation images based on different radiation energies, the system comprising: a communication unit configured to obtain at set communication intervals a temperature of a radiation tube by communication with a radiation generating unit; and a control unit configured to control, based on comparison of the temperature obtained at the communication intervals and a change rate of the temperature and respectively set threshold ranges, an operation for maintaining a driving state of the radiation tube or execution of image processing for obtaining a substance amount of a substance that forms an object using the plurality of radiation images.

Further features of the present disclosure will become apparent from the following description of exemplary embodiments (with reference to the attached drawings).

BRIEF DESCRIPTION OF THE DRAWINGS

FIG. 1 is a view illustrating a schematic configuration of a radiation imaging system.

FIG. 3 is a flowchart describing an example of operation for stabilizing the temperature state of a radiation tube.

FIG. 4 is a flowchart describing an example of operation for determining whether the temperature state of the radiation tube is stable from the pixel value of a calibration image.

FIG. 5 is a flowchart describing an example of operation for determining whether the temperature state of the radiation tube is stable from an operation status and imaging status of the radiation imaging system.

FIG. 6 is a flowchart describing an example of operation for determining whether the temperature state of the radiation tube is stable.

DESCRIPTION OF THE EMBODIMENTS

Figure 2A:
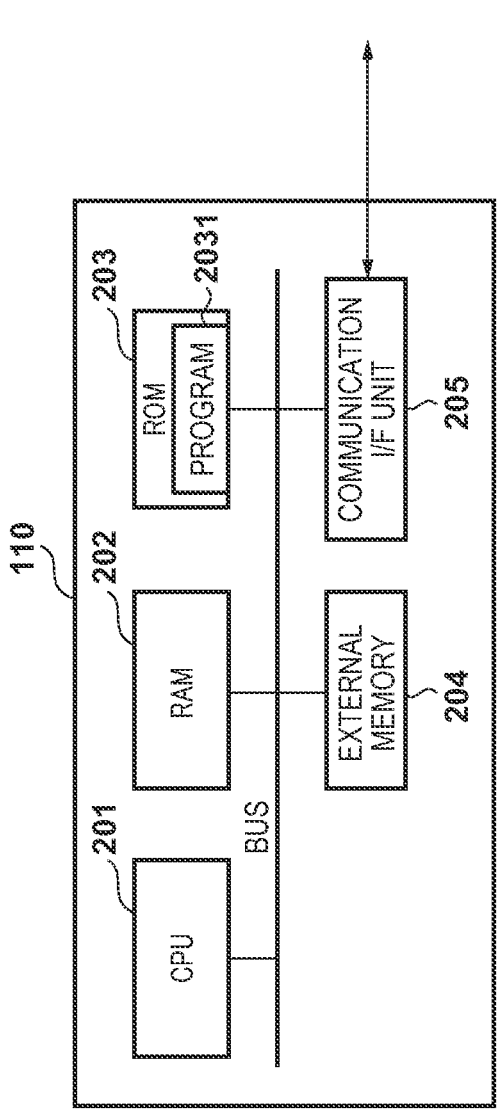
FIG. 2A is a view illustrating a hardware configuration of a control apparatus.

Hereinafter, embodiments will be described in detail with reference to the attached drawings. Note, the following embodiments are not intended to limit the scope of the claimed disclosure. Multiple features are described in the embodiments, but limitation is not made an disclosure that requires all such features, and multiple such features may be combined as appropriate. Furthermore, in the attached drawings, the same reference numerals are given to the same or similar configurations, and redundant description thereof is omitted.

First Embodiment

<1. Schematic Configuration of Radiation Imaging System>

FIG. 1 is a schematic diagram illustrating an example of a schematic configuration of a radiation imaging system 100 according to an embodiment (first embodiment) of the present disclosure. The radiation imaging system 100 comprises a control apparatus (imaging control apparatus) 110, radiation generation units (radiation generation apparatuses) 114A and 114B, radiation detectors (radiation imaging apparatuses) 115A and 115B, an RIS 130, a PACS 140, and an HIS 150. Here, RIS is an abbreviation of Radiology Information Systems. PACS is an abbreviation of Picture Archiving and Communication Systems. HIS is an abbreviation of Hospital Information Systems. Also, the radiation generation units 114A and 114B are collectively referred to in the following as radiation generation units 114 and the radiation detectors 115A and 115B are collectively referred to in the following as radiation detectors 115.

The control apparatus 110 is connected with a display unit 112, an operation unit 113, a plurality of radiation generation units 114A and 114B, and a plurality of radiation detectors 115A and 115B by wire and controls operation thereof by communicating with each of the devices. Wired communication can be performed via LAN (Local Area Network) such as Ethernet®, for example; however, communication may be performed by other communication methods. Also, the control apparatus 110 is connected with the RIS 130, the PACS 140, and the HIS 150 via a network 120 and can transmit/receive radiation images, patient information, and the like.

The display unit 112 displays imaging examination information, imaged radiation images, various kinds of information, and the like. The operation unit 113 accepts input information from an operator. In the present embodiment, the display unit 112 is a monitor (e.g., a liquid crystal display or the like), and the operation unit 113 is a keyboard, a pointing device (e.g., a mouse or the like), and a touch panel.

The radiation generation units (radiation generation apparatuses) 114A and 114B are equipped with radiation tubes that generate radiation and emit radiation in relation to patients 1000A and 1000B who are objects. The patient 1000A is in a standing position and the patient 1000B is in a supine position, and the radiation generation units 114A and 114B and the radiation detectors 115A and 115B are arranged at positions that are suitable for imaging. Note that in the present embodiment, an example in which the radiation generation units 114A and 114B are respectively installed in a room in which radiation imaging is performed as in FIG. 1 and a spatial range in which each of the radiation generation units 114 emits radiation is limited to a fixed range will be described. However, a portable one may be used as a radiation generation unit.

A plurality of radiation detectors (radiation imaging apparatuses) 115A and 115B generate an image based on radiation that was emitted from the radiation generation units 114A and 114B, respectively. The control apparatus 110 executes image processing in relation to radiation image data that was detected and obtained in the radiation detector 115A or 115B and displays the result as a radiation image on the display unit 112. The radiation detectors 115A and 115B are installed in a room or at a desk in accordance with a spatial range in which the radiation generation units 114A and 114B emit radiation.

Note that description will be given assuming that the radiation imaging system 100 according to the present embodiment includes the RIS 130, the PACS 140, and the HIS 150; however, configuration may be taken so as to not include at least some of these.

Also, FIG. 1 illustrates an example in which the radiation generation units 114A and 114B and the radiation detectors 115A and 115B exist as radiation generation units and radiation detectors; however, combination of radiation generation units and radiation detectors is not limited to this. For example, configuration may be taken so as to include further combination of radiation generation units and radiation detectors in the radiation imaging system 100.

<2. Configuration of Control Apparatus>

Next, an example of configuration of the control apparatus 110 according to the present embodiment will be described. First, FIG. 2A is a schematic diagram illustrating an example of a hardware configuration of the control apparatus 110. The control apparatus 110 comprises a CPU 201, a RAM 202, a ROM 203, an external memory 204, and a communication I/F unit 205, and these are mutually connected via a bus.

The CPU (central processing unit) 201 comprehensively controls operation of the control apparatus 110 and controls each of the configuration units (the RAM 202 to the communication I/F unit 205) illustrated in FIG. 2A via a bus.

The RAM (random access memory) 202 functions as a main memory, a work area, and the like of the CPU 201. The CPU 201, when executing processing, realizes various kinds of function operation by loading to the RAM 202 a necessary computer program 2031, base data, or the like from the ROM 203 and then executing the computer program 2031 or the like. In the ROM (read-only memory) 203, the computer program 2031, base data, and the like that are necessary for the CPU 201 to execute processing are stored. Note that the computer program 2031 may be stored in the external memory 204.

The external memory 204 is a large-capacity storage apparatus and is realized by a hard disk apparatus, an IC memory, or the like, for example. In the external memory 204, various kinds of data, information, and the like that are necessary for when, for example, the CPU 201 performs processing using the computer program 2031 or the like are stored. Also, in the external memory 204, various kinds of data, information, and the like obtained by, for example, the CPU 201 performing processing using the computer program 2031 or the like are stored.

The communication I/F (interface) unit 205 controls communication with an external unit. The bus is for communicably connecting the CPU 201, the RAM 202, the ROM 203, the external memory 204, and the communication I/F unit 205.

The control apparatus 110 according to the present embodiment is provided as a dedicated embedded device but may be realized by a general-purpose information processing apparatus such as a PC (personal computer) or a tablet terminal.

Figure 2B:
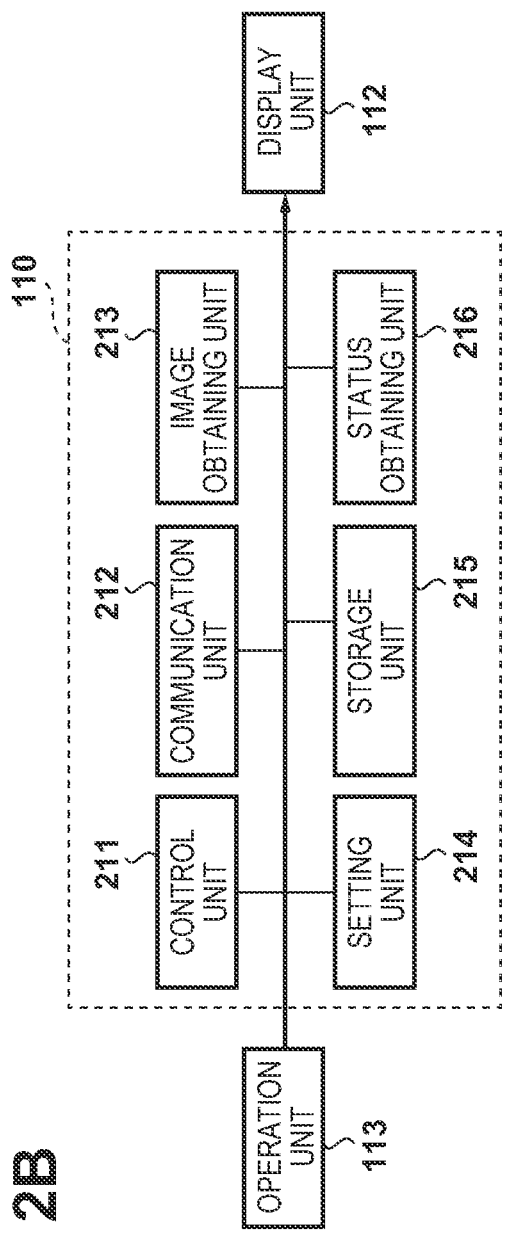
FIG. 2B is a view illustrating a software configuration of a control apparatus.

FIG. 2B is a functional block diagram illustrating a software configuration of the control apparatus 110 according to the present embodiment. The control apparatus 110 comprises a control unit 211, a communication unit 212, an image obtaining unit 213, a setting unit 214, a storage unit 215, and a status obtaining unit 216. Each of the functions is realized by the CPU 201 deploying in the RAM 202 the computer program 2031 stored in the ROM 203 and then executing it.

The control unit 211 generates and edits various kinds of setting information that is set in the radiation imaging system 100 and determines the existence/absence thereof. The communication unit 212 obtains various kinds of information by communicating with the radiation generation units 114A and 114B and the radiation detectors 115A and 115B. The image obtaining unit 213 obtains radiation images from the radiation detectors 115A and 115B.

The setting unit 214 registers and updates various kinds of setting information of the radiation imaging system 100. The storage unit 215 stores various kinds of setting information of the radiation imaging system 100, various kinds of information obtained in the communication unit 212, radiation images imaged in the past, an operation log of the radiation imaging system, and the like. The status obtaining unit 216 obtains and stores in the storage unit 215 of various kinds of operation status information of the radiation imaging system 100, an operation history of the operator, and the like.

Each of the above-described functional blocks here is at most an example, and the control apparatus 110 may be configured to not include some of each of the above-described functional blocks or may be configured to include further functional blocks.

<3. Example of Measurement Processing of Bone Mineral Amount>

FIG. 3 is a flowchart describing an example of operation for the control apparatus 110 to stabilize a temperature state of a radiation tube in the radiation imaging system 100 according to the present embodiment. Each step of FIG. 3 is executed by the CPU 201 of the control apparatus 110 controlling the radiation imaging system 100 based on the computer program 2031. The radiation imaging system 100 according to the present embodiment can obtain substance images (e.g., a soft tissue image and a bone tissue image) which were separated into a plurality of substances (e.g., soft tissue and bone tissue) that form an object using a plurality of radiation images obtained by different radiation energies and obtain bone density (a value of a bone mineral amount) as an amount of substance in bone tissue by executing image processing based on the obtained substance images.

First in step S301, the operation unit 113 receives operation content for a start of bone mineral amount measurement examination from the operator, and the control unit 211 displays an imaging screen on the display unit 112. By display control of the control unit 211, a screen display of the display unit 112 is transitioned to an imaging screen.

In step S302, the communication unit 212 obtains at fixed communication intervals preset in the setting unit 214 the temperature (temperature state) of the radiation tube by communicating with the radiation generation unit 114A or 114B.

In step S303, the setting unit 214 sets communication intervals, a threshold range of radiation tube temperature and a threshold range of temperature change rate as threshold ranges. A change rate of radiation tube temperature is calculated based on the temperature (temperature state) of the radiation tube that the control unit 211 obtained in step S302 and is compared with the temperature threshold and the temperature change rate threshold that were preset in the setting unit 214.

The control unit 211, based on the comparison between the temperature obtained at communication intervals and the temperature change rate and the respectively set threshold ranges, controls execution of operation for maintaining the driving state of the radiation tube or image processing for obtaining the amount of substance that forms the object using a plurality of radiation images.

The control unit 211, in a case where at least one of the temperature or the temperature change rate is outside the threshold range (step S303; NO), advances the processing to step S304.

In step S304, the control unit 211 executes control for maintaining the driving state of the radiation tube such that the temperature and the temperature change rate are within the respectively set threshold ranges. In order to have the temperature state of the radiation tube be at a fixed temperature or higher and the temperature change (temperature change rate) be in a stable state, the control unit 211 executes control for maintaining the driving state of the radiation tube by causing an energized state in which a fixed current is applied in relation to the radiation tube or a non-energized state in which the current applied in relation to the radiation tube is stopped and then advances the processing to step S302.

Meanwhile, in a case where the temperature of the radiation tube and the temperature change rate are within the threshold (temperature threshold and temperature change rate threshold) ranges in step S303 (step S303; YES), the control unit 211 determines that the temperature state of the radiation tube has stabilized and then ends the processing.

Each of the processing of the flowchart in FIG. 3 is thus ended. After this processing, two radiation beams of different energy distribution are generated from one of the radiation generation units of either the radiation generation units 114A or 114B in accordance with the operation of the operator in relation to the operation unit 113. The generated radiation beams pass through the object and are captured in one of the radiation detectors of either the radiation detectors 115A or 115B, and the control unit 211 measures a bone mineral amount from a difference between soft tissue and bone tissue radiation absorption coefficients that were detected based on the captured radiation image.

Specifically, the control unit 211 uses an energy subtraction method in which new images (e.g., a bone tissue image and a soft tissue image) are obtained by processing a plurality of radiation images whose energies of radiation emitted onto the object are different. In a case of executing imaging by the energy subtraction method, at least two radiation images captured at different radiation energies will be necessary in order to generate one subtraction image. For example, one of the radiation detectors 115 of either the radiation detectors 115A or 115B performs a plurality of samplings in relation to a single radiation emission. By this, the radiation detector 115 can obtain an image by low-energy radiation (low-energy radiation image) and an image by high-energy radiation (high-energy radiation image) in a single radiation emission. Capturing by the radiation detectors 115 may be still image capturing or moving image capturing.

The radiation distribution information temporarily stored within the radiation detectors 115 can be read out after sampling and holding execution, and the control unit 211 executes readout of radiation distribution information (XL) and radiation distribution information (XL+XH) at different timings from the radiation detectors 115. The control unit 211, by subtracting the radiation distribution information (XL) from the radiation distribution information (XL+XH), can obtain the radiation distribution information (XH). Here, the low-energy radiation distribution information (XL) will be the base image of a low-energy radiation image, and the high-energy radiation distribution information (XH) will be the base image of a high-energy radiation image.

The control apparatus 110, by solving simultaneous equations using a high-energy radiation image (XH) and a low-energy radiation image (XL) which were captured in the radiation detector 115 and a radiation absorption coefficient (e.g., a linear attenuation coefficient or mass attenuation coefficient) of each of the substances in high energy and low energy, obtains substance images (e.g., a soft tissue image and a bone tissue image) which were separated into substances (soft tissue and bone tissue) that forms the object.

Substance images are images that, in a case where the object is represented in two or more specific substances, are separated into two or more images formed by a thickness or density of that substance. In a case where a linear attenuation coefficient is used as a radiation absorption coefficient of each of the substances, it is possible to obtain an image that illustrates a distribution of a thickness of each of the substances. In a case where a mass attenuation coefficient is used as a radiation absorption coefficient, it is possible to obtain an image that illustrates a distribution of density of each of the substances.

The control unit 211, regarding a plurality of substances that form the object, obtains amounts of substances by image processing which uses respectively different radiation absorption coefficients and a plurality of radiation images (a low-energy radiation image and a high-energy radiation image). The control unit 211 obtains bone density (a value of a bone mineral amount) as a substance amount of bone tissue by image processing which uses a radiation absorption coefficient (a mass attenuation coefficient) of soft tissue and a radiation absorption coefficient (a mass attenuation coefficient) of bone tissue that form the object and a plurality of radiation images.

As described above, the control apparatus 110 according to the present embodiment, in imaging for when measuring bone mineral amount, obtains the temperature state of the radiation tube from the radiation generation units 114A or 114B at preset fixed communication intervals. Here, the control apparatus 110, in a case where at least one of the temperature of the radiation tube or the temperature change rate is outside the threshold range, performs control for maintaining the driving state of the radiation tube. Specifically, the control unit 211, as control for maintaining the driving state of the radiation tube, performs control for causing the radiation tube to be in an energized state or control such as causing the radiation tube to be in a non-energized state.

By maintaining the driving state of the radiation tube as such, it is possible to stabilize the temperature state so as not to change. In other words, it becomes impossible to execute imaging of a radiation image for measuring a bone mineral amount until the temperature state of the radiation tube stabilizes.

By virtue of the present embodiment, it becomes possible to reduce an effect on the measurement accuracy of a substance amount obtained by image processing based on radiation images that may be caused by a difference in the temperature state of the radiation tube. By this, it becomes possible, in imaging for when measuring a bone mineral amount, to reduce an effect on accuracy of a bone mineral amount measurement result that may be caused by a difference in the temperature state of the radiation tube.

Second Embodiment

In the first embodiment, an example of processing for obtaining the temperature state of the radiation tube from the radiation generation unit and stabilizing the temperature state was described. In contrast to this, in the second embodiment, an example of determining whether the temperature state of the radiation tube is stable from a pixel value of a calibration image will be described. Note that the configuration of the radiation imaging system, the control apparatus, and the like according to the present embodiment is the same as the first embodiment; accordingly, detailed description will be omitted.

Generally, there may arise cases where the temperature state of the radiation tube cannot be obtained in the communication between the control apparatus 110 and the radiation generation units 114A and 114B. For example, in the example of FIG. 1, these are cases where communication of temperature state information of the radiation tube has not been envisioned for one of the radiation generation units 114A and 114B and the control apparatus 110, such as in a case where the respective manufacturing companies of the radiation generation units 114A and 114B and the control apparatus 110 are different, and the like.

Accordingly, in the present embodiment, the control apparatus 110 determines whether the temperature state of the radiation tube is stable from a pixel value of a calibration image.

In imaging for when measuring bone mineral amount, a calibration screen is first transitioned to, and calibration is executed. It is determined whether or not the temperature state of the radiation tube is stable from comparison of a pixel value of an obtained calibration image and a pixel value of a preset reference image. In other words, if a difference in comparison of a pixel value of a calibration image and a pixel value of a reference image is within a set threshold range, an effect on accuracy of bone mineral amount measurement result calculation will also be small. Accordingly, even in a case where the temperature state of the radiation tube cannot be obtained from the radiation generation unit, it is possible to expect that an effect on accuracy of a bone mineral amount measurement result is reduced.

FIG. 4 is a flowchart describing an example of operation for the control apparatus 110 to determine whether the temperature state of the radiation tube is stable from a pixel value of a calibration image in the radiation imaging system 100 according to the second embodiment.

Each step of FIG. 4 is executed by the CPU 201 of the control apparatus 110 controlling the radiation imaging system 100 based on the computer program 2031.

First in step S401, the operation unit 113 receives operation content for a start of bone mineral amount measurement examination from the operator, and the control unit 211 displays the calibration screen on the display unit 112. By display control of the control unit 211, a screen display of the display unit 112 is transitioned to a calibration screen.

In step S402, by a calibration operation by the operator in the operation unit 113, calibration of the radiation imaging system 100 is executed.

In step S403, by execution of calibration of the radiation imaging system 100 (the radiation generation units 114 and the radiation detectors 115) that the image obtaining unit 213 executed in step S402, a calibration image and a pixel value of that image are obtained.

In step S404, the control unit 211 compares the pixel value of the calibration image that the image obtaining unit 213 obtained in step S403 and a pixel value, which is a reference, (reference pixel value) of the reference image preset in the setting unit 214. The setting unit 214 sets a threshold range in order to determine whether the temperature state of the radiation tube is stable.

In step S405, the control unit 211 determines whether difference between pixel value of the calibration image and the reference pixel value compared in step S404 is within the threshold range preset in the setting unit 214.

The control unit 211, based on comparison of the difference between the pixel value of the calibration image and the pixel value of the reference image and the threshold range set for determining whether the temperature state of the radiation tube is stable, controls continuation of calibration execution or execution of image processing for obtaining the amount of substance that forms the object using a plurality of radiation images.

In a case where the difference in pixel values is outside the threshold range (step S405; NO), the processing advances to step S402, and calibration execution is continued again. In other words, the control unit 211, in a case where difference between the pixel value of the calibration image and the pixel value of the reference image is outside the set threshold range, advances the processing to step S402 and continues calibration execution such that difference in pixel values will be within the threshold range.

Meanwhile, the control unit 211, in a case where the difference in pixel values is within the threshold range (step S405; YES), determines that the temperature state of the radiation tube is stable (i.e., if the difference between the pixel value of the calibration image and the pixel value of the reference image is within the set threshold range, will determine that an effect on accuracy of a bone mineral amount measurement result can be reduced) and advances the processing to step S406.

In step S406, the control unit 211 displays the imaging screen on the display unit 112 and then ends the processing. By display control of the control unit 211, a screen display of the display unit 112 is transitioned from the calibration screen to the imaging screen.

Each of the processing of the flowchart in FIG. 4 is thus ended. After this processing, two radiation beams of different energy distribution are generated from one of the radiation generation units of either the radiation generation units 114A or 114B in accordance with the operation of the operator in relation to the operation unit 113. The generated radiation beams pass through the object and are captured in one of the radiation detectors of either the radiation detectors 115A or 115B, and the control unit 211 measures a bone mineral amount from a difference between soft tissue and bone tissue radiation absorption coefficients that were detected based on the captured radiation image.

The control apparatus 110 according to the present embodiment, in imaging for when measuring a bone mineral amount, executes calibration in advance and compares the pixel value of the calibration image and the pixel value of the preset reference image. Here, the control apparatus 110, in a case where the difference between the pixel value of the calibration image and the pixel value of the reference image is outside the threshold range set for determining whether the temperature state of the radiation tube is stable, continues to execute calibration.

By repeatedly executing calibration as described above, it is possible to have the difference between the pixel value of the calibration image and the pixel value of the reference image within the fixed threshold range.

By this, it becomes possible, in imaging for when measuring a bone mineral amount, to reduce an effect on accuracy of a bone mineral amount measurement result that may be caused by a difference in the temperature state of the radiation tube.

Third Embodiment

In the second embodiment, an example of processing for determining whether the temperature state of the radiation tube is stable from a pixel value of a calibration image was described. In contrast to this, in the third embodiment, an example of determining whether the temperature state of the radiation tube is stable from an operation status and imaging status of the radiation imaging system will be described. Note that the configuration of the radiation imaging system, the control apparatus, and the like according to the present embodiment is the same as the first embodiment; accordingly, detailed description will be omitted.

Generally, it is common for the radiation imaging system to be put in an operating state in advance prior to imaging even in imaging that is not by bone mineral amount measurement and it is common to have already been executing imaging of another examination. In such cases, it is common for the temperature of the radiation tube to be at a fixed temperature or higher in comparison to a state immediately after the radiation imaging system was put in an operating state.

Accordingly, in the present embodiment, it is determined whether the temperature state of the radiation tube is stable from an operation status and imaging status of the radiation imaging system.

In other words, imaging for bone mineral amount measurement becomes possible in a case where an operation status and imaging status of the radiation imaging system when imaging by bone mineral amount measurement was executed in the past and the current operation status and imaging status are compared and it is determined that an effect on accuracy of a bone mineral amount measurement result will be reduced. Accordingly, it ceases to be necessary to execute calibration, and it becomes possible to prevent imaging efficiency from lowering in imaging by bone mineral amount measurement.

FIG. 5 is a flowchart describing an example of operation for the control apparatus 110 to determine whether the temperature state of the radiation tube is stable from an operation status of the radiation imaging system 100 and the number of imagings in the radiation imaging system 100 according to the third embodiment. The processing that is the same as in FIG. 4 is assigned the same reference numeral and description will be omitted. Each step of FIG. 5 is executed by the CPU 201 of the control apparatus 110 controlling the radiation imaging system 100 based on the computer program 2031.

First in step S501, the operation unit 113 receives operation content for a start of bone mineral amount measurement examination from the operator, and the status obtaining unit 216 obtains the current operation information of the radiation imaging system 100. The status obtaining unit 216 obtains as current operation information an operation duration from activation of the radiation imaging system 100 until obtainment of current operation information. The status obtaining unit 216 activates a timer at a time of activation of the radiation imaging system 100. The status obtaining unit 216 obtains the operation duration of the radiation imaging system 100 as a duration, for example, from activation of the radiation imaging system 100 until obtainment of the current operation information (a start of bone mineral amount measurement examination). Also, the status obtaining unit 216, based on operation log information of the radiation imaging system 100 stored in the storage unit 215, may obtain as the operation duration a duration from activation of the radiation imaging system 100 until an operation log of a start of bone mineral amount measurement examination.

In step S502, the status obtaining unit 216, as the current operation information, obtains the number of imagings in the operation duration from activation of the radiation imaging system 100 until obtainment of the current operation information (a start of bone mineral amount measurement examination). Here, the status obtaining unit 216, based on, for example, the operation log information of the radiation imaging system 100 that is stored in the storage unit 215, may obtain the number of imagings.

In step S503, the control unit 211 determines whether the temperature state of the radiation tube is stable based on the current operation information obtained in steps S501 and S502.

The storage unit 215 stores past operation information obtained in the status obtaining unit 216. For example, with a start of the current bone mineral amount measurement examination as a starting point, in a plurality of bone mineral amount measurements performed in the past, past operation information such as the operation duration and the number of imagings obtained in the status obtaining unit 216 is stored in the storage unit 215.

The control unit 211, by statistical processing of past operation information (an operation duration and the number of imagings), obtains statistical distribution (e.g., a normal distribution) that indicates operation information variability and, as a range in which the temperature state of the radiation tube is stable, a range (threshold range of statistical distribution) that is specified by a predetermined deviation (e.g., parameters such as standard deviation σ, 2σ, 3σ . . . ) from a reference value of statistical distribution (e.g., an average value or a median value).

The control unit 211, in a statistical distribution that indicates operation information variability obtained by performing statistical processing on the past operation information, determines whether the current operation information is included in a threshold range of statistical distribution in which the temperature state of the radiation tube is stabilized. Then, the control unit 211, in a case where the current operation information is included in the threshold range, executes image processing for obtaining the amount of substance that forms the object using a plurality of radiation images.

In other words, the control unit 211, in a case where the current operation information obtained in steps S501 and S502 are included in the threshold range of statistical distribution in which the temperature state of the radiation tube is stabilized (step S503; Yes), determines that the temperature (temperature state) of the radiation tube is stable and advances the processing to step S406. In step S406, the control unit 211 displays the imaging screen on the display unit 112 and then ends the processing. Then, the control unit 211 executes image processing (bone mineral amount measurement processing) for obtaining the amount of substance that forms the object using a plurality of radiation images.

Meanwhile, in a case where the current operation information obtained in steps S501 and S502 is outside the threshold range of statistical distribution, the control unit 211 determines that the temperature (temperature state) of the radiation tube is not stable (step S503; No) and advances the processing to step S401. In other words, in a case where at least one of the operation duration and the number of imagings is not included in the threshold range of statistical distribution as the current operation information, the control unit 211 determines that the temperature (temperature state) of the radiation tube is not stable and advances the processing to step S401.

The processing content of step S401 and subsequent steps are the same as the second embodiment, and calibration is executed prior to imaging for bone mineral amount measurement and the pixel value of the calibration image and the pixel value of the preset reference image are compared. The control unit 211 of the control apparatus 110, in a case where difference between the pixel value of the calibration image and the pixel value of the reference image is outside the set threshold range, advances the processing to step S402 and continues calibration execution such that difference in pixel values will be within the threshold range. Meanwhile, in a case where the difference in pixel values is within the threshold range (step S405; Yes), the control apparatus 110 determines that the temperature state of the radiation tube is stable, causes the display unit 112 to transition to the imaging screen (step S406), and transitions to imaging of a radiation image in order to obtain a value of a bone mineral amount. Each of the processing of the flowchart in FIG. 5 is thus ended.

As described above, in the third embodiment, it is possible to determine whether the temperature state of the radiation tube is stable based on a result that was statistically analyzed based on the operation duration of the radiation imaging system and the number of imagings. In a case where the temperature state of the radiation tube is a stable state, it is unnecessary to execute calibration prior to radiation imaging for bone mineral amount measurement. By this, it becomes possible to reduce an effect on accuracy of a bone mineral amount measurement result that may be caused by a difference in the temperature state of the radiation tube and achieve an improvement in efficiency of bone mineral amount measurement.

Fourth Embodiment

In the fourth embodiment, an example of operation of the radiation imaging system 100 in which each of the processing described in the first embodiment to the third embodiment have been combined will be described.

FIG. 6 is a flowchart illustrating an example of operation for the control apparatus 110 to determine whether the temperature state of the radiation tube is stable in the radiation imaging system 100 according to the fourth embodiment. The processing that is the same as in FIG. 3 to FIG. 5 is assigned the same reference numeral and detailed description will be omitted. Each step of FIG. 6 is executed by the CPU 201 of the control apparatus 110 controlling the radiation imaging system 100 based on the computer program 2031.

First in step S601, the operation unit 113 receives operation content for a start of bone mineral amount measurement examination from the operator, and the control unit 211 determines whether it is possible to obtain the temperature state of the radiation tube. In case where the control unit 211 determines that it is not possible to obtain the temperature state of the radiation tube in the determination processing in step S601 (step S601; No), the processing advances to step S501. Meanwhile, in case where the control unit 211 determines that it is possible to obtain the temperature state of the radiation tube in the determination processing in step S601 (step S601; No), the processing advances to step S302.

The processing in steps S302 and S303 are the same as in FIG. 3 (first embodiment). In the present embodiment, in a case where the temperature of the radiation tube and the temperature change rate are within the threshold (temperature threshold and temperature change rate threshold) ranges in the determination processing in step S303 (step S303; YES), the control unit 211 determines that the temperature state of the radiation tube is stable and advances the processing to step S406.

Meanwhile, in a case where at least one of the temperature of the radiation tube and the temperature change rate is outside the threshold (temperature threshold and temperature change rate threshold) range in the determination processing in step S303 (step S303; NO), the control unit 211 advances the processing to step S501.

The processing in steps S501 to S503 are the same as in FIG. 5 (third embodiment). In step S503, the control unit 211 determines whether the temperature state of the radiation tube is stable based on the current operation information obtained in steps S501 and S502.

In a case where the control unit 211 determines that the temperature (temperature state) of the radiation tube is stable in the determination processing in step S503 (step S503; Yes), the processing advances to step S406. Meanwhile, in a case where the control unit 211 determines that the temperature (temperature state) of the radiation tube is not stable in the determination processing in step S503 (step S503; No), the processing advances to step S401.

The processing in steps S401 to S406 are the same as in FIG. 4 (second embodiment). In the determination processing in step S405, the control unit 211 determines whether difference between the pixel value of the calibration image and the pixel value of the reference image compared in step S404 is within the threshold range preset in the setting unit 214.

In a case where the difference in pixel values is outside the threshold range (step S405; NO), the processing advances to step S402, and execution of calibration is continued again. Meanwhile, in a case where difference between pixel value of the calibration image and the reference pixel value is within the threshold range in the determination processing in step S405 (step S405; YES), the control unit 211 determines that the temperature (temperature state) of the radiation tube is stable and advances the processing to step S406. In step S406, the control unit 211 displays the imaging screen on the display unit 112 and then ends the processing.

By virtue of each embodiment of the present disclosure, it becomes possible to provide a radiation imaging technique that is capable of reducing, in imaging for measuring a bone mineral amount, an effect on accuracy of a bone mineral amount measurement result that may be caused by a difference in the temperature state of the radiation tube.

By virtue of each embodiment of the present disclosure, it becomes possible to reduce an effect on the measurement accuracy of a substance amount obtained by image processing based on radiation images that may be caused by a difference in the temperature state of the radiation tube.

By this, it becomes possible, in imaging of radiation images for when measuring a bone mineral amount, to reduce an effect on accuracy of a bone mineral amount measurement result that may be caused by a difference in the temperature state of the radiation tube.

Other Embodiments

Embodiment(s) of the present disclosure can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present disclosure has been described with reference to exemplary embodiments, the scope of the following claims are to be accorded the broadest interpretation so as to encompass all such modifications and equivalent structures and functions.

This application claims the benefit of Japanese Patent Application No. 2020-113190, filed Jun. 30, 2020, which is hereby incorporated by reference herein in its entirety.

What is claimed is:

1. A radiation imaging system operable to generate a plurality of radiation images based on different radiation energies, the system comprising:
   at least one processor; and
   at least one memory storing a program including instructions executed by the at least one processor,
   wherein the at least one processor and the at least one memory being operatively coupled to function as:
   a communication unit configured to obtain at set communication intervals a temperature of a radiation tube by communication with a radiation generating unit; and
   a control unit configured to control, based on comparison of the temperature obtained at the communication intervals and a change rate of the temperature and respectively set threshold ranges, an operation for maintaining a driving state of the radiation tube or execution of image processing for obtaining a substance amount of a substance that forms an object using the plurality of radiation images.

2. The radiation imaging system according to claim 1, wherein the control unit, in a case where at least one of the temperature and the change rate of the temperature are outside the threshold ranges, executes control for maintaining the driving state of the radiation tube such that the temperature and the change rate of the temperature are within the threshold ranges.

3. The radiation imaging system according to claim 1, wherein the control unit executes control for maintaining the driving state of the radiation tube by causing an energized state in which a fixed current is applied in relation to the radiation tube or a non-energized state in which a current applied in relation to the radiation tube is stopped.

4. The radiation imaging system according to claim 1, wherein the at least one processor and the at least one memory being operatively coupled to function as: a setting unit configured to set the communication interval and, as the threshold ranges, a threshold range of the temperature of the radiation tube and a threshold range of the change rate of the temperature.

5. A radiation imaging system operable to perform image processing based on a plurality of radiation images based on different radiation energies, the system comprising:
   at least one processor; and
   at least one memory storing a program including instructions executed by the at least one processor,
   wherein the at least one processor and the at least one memory being operatively coupled to function as:
   an image obtaining unit configured to obtain a pixel value of a calibration image generated by calibration of the radiation imaging system; and
   a control unit configured to, based on comparison of a difference between the pixel value of the calibration image and a pixel value of a reference image and a threshold range set for determining whether a temperature state of a radiation tube is stable, controls continuation of calibration execution or execution of image processing for obtaining an amount of a substance that forms an object using a plurality of radiation images.

6. The radiation imaging system according to claim 5, wherein the control unit, in a case where the difference is outside the threshold range, continues execution of the calibration such that the difference is within the threshold range.

7. The radiation imaging system according to claim 5, wherein, wherein the at least one processor and the at least one memory being operatively coupled to function as: a setting unit configured to set the threshold range in order to determine whether the temperature state of the radiation tube is stable.

8. A radiation imaging system operable to generate a plurality of radiation images based on different radiation energies, the system comprising:
at least one processor; and
at least one memory storing a program including instructions executed by the at least one processor,
wherein the at least one processor and the at least one memory being operatively coupled to function as:
a status obtaining unit configured to obtain current operation information of the radiation imaging system;
a storage unit configured to store past operation information of the radiation imaging system; and
a control unit configured to, in a statistical distribution that indicates operation information variability obtained by performing statistical processing on the past operation information, determines whether the current operation information is included in a statistical distribution threshold range in which a temperature state of a radiation tube is stabilized, and in a case where the current operation information is included in threshold range, uses the plurality of radiation images to execute image processing for obtaining an amount of a substance forming an object.

9. The radiation imaging system according to claim 8, wherein the status obtaining unit obtains, as the current operation information, an operation duration from activation of the radiation imaging system until obtainment of the operation information and the number of imaging s in the operation duration.

10. The radiation imaging system according to claim 9, wherein the control unit, in a case where the operation duration and the number of imagings are included in the threshold range of the statistical distribution, executes the image processing.

11. The radiation imaging system according to claim 9, wherein the at least one processor and the at least one memory being operatively coupled to function as: an image obtaining unit configured to obtain a pixel value of a calibration image generated by calibration of the radiation imaging system,
wherein, in a case where at least one of the operation duration and the number of imagings is not included in the threshold range of the statistical distribution, the control unit,
based on comparison of a difference between the pixel value of the calibration image and the pixel value of a reference image and the threshold range set for determining whether the temperature state of the radiation tube is stable, controls continuation of calibration execution or execution of image processing.

12. The radiation imaging system according to claim 11, wherein the control unit, regarding a plurality of substances that form the object, obtains an amount of the substances by the image processing that uses respectively different radiation absorption coefficients and the plurality of radiation images.

13. The radiation imaging system according to claim 12, wherein the control unit, by image processing using a radiation absorption coefficient of a soft tissue that forms the object and a radiation absorption coefficient of a bone tissue that forms the object and the plurality of radiation images, obtains a bone density as a substance amount of the bone tissue.

14. A control apparatus comprising:
at least one processor; and
at least one memory storing a program including instructions executed by the processor,
wherein the at least one processor and the at least one memory being operatively coupled to function as:
a communication unit configured to obtain a temperature of a radiation tube by communication with a radiation generating unit; and
a control unit configured to control, based on comparison of the temperature and a predetermined range, to a state in which imaging related to a plurality of radiation images based on different radiation energies is possible.

15. A control apparatus operable to control a radiation imaging system that performs image processing based on a plurality of radiation images based on different radiation energies, the control apparatus comprising:
at least one processor; and
at least one memory storing a program including instructions executed by the processor,
wherein the at least one processor and the at least one memory being operatively coupled to function as:
an image obtaining unit configured to obtain a pixel value of a calibration image generated by calibration of the radiation imaging system; and
a control unit configured to, based on comparison of a difference between the pixel value of the calibration image and the pixel value of a reference image and a threshold range set for determining whether a temperature state of a radiation tube is stable, controls continuation of calibration execution or execution of image processing for obtaining an amount of a substance that forms an object using a plurality of radiation images.

16. A control apparatus operable to control a radiation imaging system for generating a plurality of radiation images based on different radiation energies, the system comprising:
at least one processor; and
at least one memory storing a program including instructions executed by the processor,
wherein the at least one processor and the at least one memory being operatively coupled to function as:
a status obtaining unit configured to obtain current operation information of the radiation imaging system;
a storage unit configured to store past operation information of the radiation imaging system; and
a control unit configured to, in a statistical distribution that indicates operation information variability obtained by performing statistical processing on the past operation information, determines whether the current operation information is included in a statistical distribution threshold range in which a temperature state of a radiation tube is stabilized, and in a case where the current operation information is included in threshold range, uses the plurality of radiation images to execute image processing for obtaining an amount of a substance forming an object.

17. A control method comprising:
obtaining a temperature of a radiation tube by communication with a radiation generating unit; and
controlling, based on a comparison of the temperature and a predetermined range, to a state in which imaging related to a plurality of radiation images based on different radiation energies is possible.

18. A method for controlling a radiation imaging system for performing image processing based on a plurality of radiation images based on different radiation energies, the method comprising:
obtaining a pixel value of a calibration image generated by calibration of the radiation imaging system; and
based on comparison of a difference between the pixel value of the calibration image and the pixel value of a reference image and a threshold range set for determining whether a temperature state of a radiation tube is stable, controls continuation of calibration execution or execution of image processing for obtaining an amount of substance that forms an object using a plurality of radiation images.

19. A method for controlling a radiation imaging system operable to generate a plurality of radiation images based on different radiation energies, the method comprising:
obtaining current operation information of the radiation imaging system;
storing, in a storage unit, past operation information of the radiation imaging system; and
in a statistical distribution that indicates operation information variability obtained by performing statistical processing on the past operation information, determining whether the current operation information is included in a statistical distribution threshold range in which a temperature state of a radiation tube is stabilized, and in a case where the current operation information is included in threshold range, using the plurality of radiation images to execute image processing for obtaining an amount of a substance forming an object.

20. A non-transitory computer readable storage medium storing a program for causing a computer to function as each unit comprising:
a communication unit configured to obtain a temperature of a radiation tube by communicating with a radiation generating unit; and
a control unit configured to control, based on a comparison of the temperature and a predetermined range, to a state in which imaging related to a plurality of radiation images based on different radiation energies is possible.

* * * * *